United States Patent [19]

Twentier

[11] 4,088,133
[45] May 9, 1978

[54] ELECTRODE FOR ELECTROSURGICAL PROCEDURE

[75] Inventor: Max E. Twentier, Phoenix, Ariz.

[73] Assignee: Products International Company, Phoenix, Ariz.

[21] Appl. No.: 722,635

[22] Filed: Sep. 13, 1976

[51] Int. Cl.$^2$ .............................................. A61N 3/06
[52] U.S. Cl. ................................ 128/303.13; 128/418
[58] Field of Search .................. 128/303.13, 404, 410, 128/411, 416, 417, 418, 2.06 E, 2.1 E, DIG. 4, 169, 327; 174/110 F; 338/99, 100, 210, 223-225, 238; 339/DIG. 3; 40/21 C

[56] References Cited

U.S. PATENT DOCUMENTS

| | | | |
|---|---|---|---|
| 3,153,869 | 10/1964 | Twentier | 40/21 C |
| 3,233,608 | 2/1966 | Scaler, Jr. | 128/169 |
| 3,386,067 | 5/1968 | Costanzo | 338/100 |
| 3,398,233 | 8/1968 | Lizasoain | 338/210 X |
| 3,606,881 | 9/1971 | Woodson | 128/2.06 E |
| 3,612,061 | 10/1971 | Collins | 128/418 |
| 3,848,600 | 11/1974 | Patrick, Jr. et al. | 128/303.13 |
| 3,895,635 | 7/1975 | Justus et al. | 128/303.13 |
| 3,911,906 | 10/1975 | Reinhold, Jr. | 128/2.06 E |
| 3,930,506 | 1/1976 | Overend | 128/327 |

FOREIGN PATENT DOCUMENTS

| | | | |
|---|---|---|---|
| 13,888 | 10/1971 | Australia | 128/418 |
| 2,414,584 | 10/1975 | Germany | 128/303.13 |

Primary Examiner—Robert W. Michell
Assistant Examiner—Lee S. Cohen
Attorney, Agent, or Firm—Christie, Parker & Hale

[57] ABSTRACT

An indifferent electrode for use in electrosurgical procedures comprises a sheet of conductive foam conformable to body surfaces and an electrical terminal carried by the sheet of conductive foam. The electrical terminal forms an external terminal part of the electrode with which a detachable electrical connection with an electrosurgical generator can be effected.

An elongated strip connected to the sheet of conductive foam is provided for maintaining the sheet of conductive foam in direct contact with body surfaces. The elongated strip, which can be mounted around a body member, has an adhesive surface at one end of its exterior surface for adherence to an interior surface of the strip.

12 Claims, 4 Drawing Figures

ELECTRODE FOR ELECTROSURGICAL PROCEDURE

BACKGROUND

As far back as 1919, Iredell and Turner developed surgical diathermy, wherein current used to sever tissue is conducted to ground by the use of an indifferent electrode, also called a patient ground plate. Iredell and Turner demonstrated the effectiveness of a large, 72 square inch ground plate, where electrolytes, e.g. conductive pastes, gels or saline solutions are used at the skin/ground plate interface to lower resistance. The combination of a large ground plate with electrolytes is used to provide a low current density path to complete the electrosurgical circuit and minimize tissue heating at the skin/plate interface.

Large ground plates have drawbacks. They are not easily contoured to the body, and thus, relatively few body surface areas can accommodate them. When placed under a patient, for instance, it is difficult to know whether substantial plate/body contact is being maintained, particularly when the patient moves or is moved. Depending upon area contacted and method of applying the ground plate, circulation can be adversely affected, thus increasing the possibility of burns. The stiffness of plates and their infexibility and sharp edges can cause substantial discomfort to the patient, especially in the case of a prolonged operation. Also, a large patient ground plate inherently increases the possibility of accidental contact with surgical instruments or other metal objects that can result in a burn to the patient.

U.S. Pat. No. 3,848,600 issued to Patrick et al discloses a small electrode for use in electrosurgical procedures. This electrode comprises a metallic snap fastener terminal held spaced apart from the body by a polyurethane pad impregnated with a conductive electrolyte gel pad. The pad is held against the skin by a resilient sheet of foam plastic having a medical grade acrylic pressure sensitive adhesive coating on it for contact with the skin. U.S. Pat. No. 3,848,600 discloses many references of interest to electrosurgical procedures. That listing of references is herein incorporated by reference.

Although the small electrode of Patrick et al overcomes problems associated with the use of large surface area electrodes, their electrode does have disadvantages and inconveniences. The primary disadvantage resides in the utilization of the electrolytic gel which requires that the electrode be packaged individually with the gel in a liquid-tight container. This increased the over-all cost of the electrode due to the increases cost of packaging. Moreover, any premature exposure of the packaged electrode to atmospheric moisture conditions can result in the drying out of the gel. In use, gels are difficult and messy to apply, the during extended surgery, they can dry up and thereby lead to burns and other complications.

In addition to the above application disadvantages, the use of an electrolyte gel in contact with the skin, especially for long periods of time, can cause skin irritation and sores to develop. Another possible source of skin irritation during use of electrodes like that of Patrick et al is the adhesive which contacts a large area of the skin surrounding the area of the electrolyte contact. Thus, with electrodes of this type, the total skin contact area subject to irritation is substantially greater than the area to which the electrical connection is made since the area of electrical contact is separate and distinct from the area of securement. Moreover, because of this separation, the area of electrode contact is capable of surface to surface shifting which can impede the progress of the electrosurgical procedure.

Therefore, there is a need for an indifferent electrode for use with electrosurgical procedures which does not require the use of electrolytes such as conductive pastes, gels or saline solutions, which is relatively small in size and easily contoured toward various body surfaces to allow application to many sites, and which can be maintained securely attached to body surfaces without direct application of adhesives to body surfaces.

SUMMARY OF THE INVENTION

This invention relates to an indifferent electrode having the above features for use in electrogurical procedures with an electrosurgical generator. The electrode comprises a sheet of conductive foam conformable to body surfaces and an electrical terminal means such as a metallic snap fastener carried by the sheet of conductive foam. The electrical terminal means forms an exterior terminal part of the electrode with which a detachable electrical connection with an electrosurgical generator can be effected. Means connected to the sheet of conductive foam are provided for maintaining the sheet of conductive foam in direct intimate contact with body surfaces.

The conductive foam can comprise polyurethane foam containing fine conductive particles such as carbon particles. Sufficient conductive particles are provided in the sheet of conductive foam so that it has a resistivity less than about 4,000 ohm-centimeters (ohm-cm), and more preferably a resistivity of less than about 2,500 ohm-cm to provide a low current density path to complete the electrosurgical circuit.

The means for maintaining the conductive foam in direct contact with body surfaces can be an elongated flexible strip secured to the exterior surface of the sheet of conductive foam. The strip, which can be mounted around a body member, has an adhesive surface at one end of its exterior surface for attachment to the interior surface of the strip, which is susceptible to adherence to the adhesive surface.

DRAWINGS

These and other features and aspects of the advantages of the present invention become more apparent with reference to the following description, appended claims and accompanying drawings where:

DESCRIPTION

Figure 1:
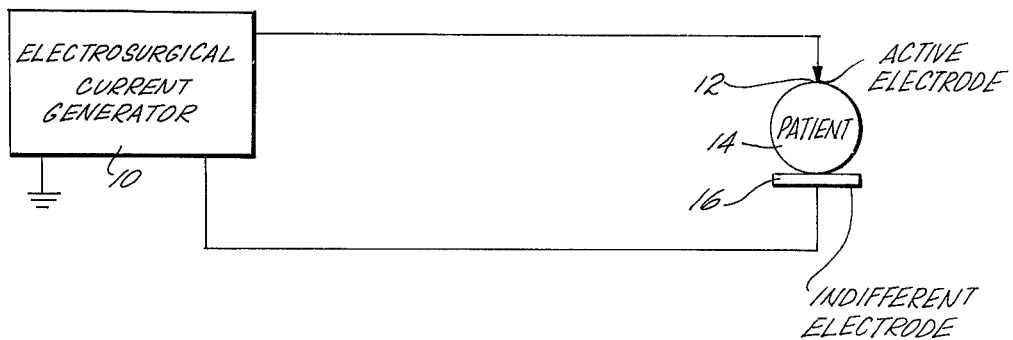
FIG. 1 is a schematic view of an electrosurgical current source, active electrode, patient, and indifferent electrode.

With reference to FIG. 1, an electrosurgical generator 10 provides a high frequency electric current which is fed to an active electrode 12 used to cut tissue and coagulate blood vessels of a patient 14. To complete the circuit an indifferent electrode 16 in direct contact with the patient is provided.

The indifferent electrode 16 comprises a sheet of conductive foam conformable to body surfaces and electrical terminal means carried by the sheet of conductive foam. The electrical terminal means forms an exterior terminal part of the electrode with which a detachable electrical connection with the electrosurgical generator can be effected. Means connected to the sheet of conductive foam are provided for maintaining the sheet of conductive foam in direct contact with body surfaces.

Figure 2:
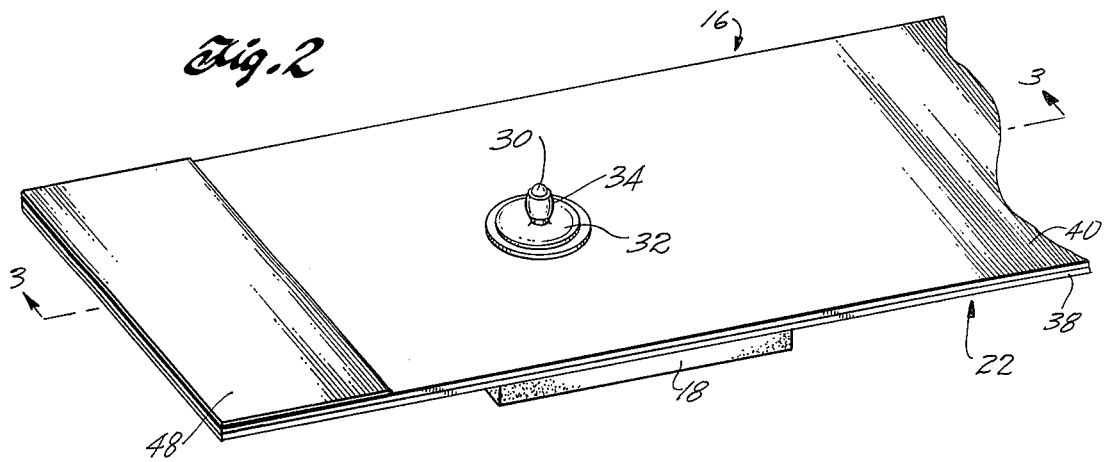
FIG. 2 is a perspective view of an electrode having features of this invention.
Figure 3:
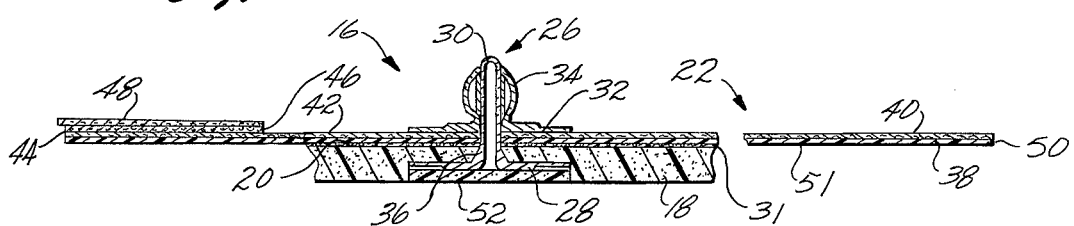
FIG. 3 is a cross-sectional view of the electrode of FIG. 2 taken along line 3—3 of FIG. 2.

With reference to FIGS. 2 and 3, an indifferent electrode embodying features of this invention comprises a substantially rectangular, flexible and resilient sheet 18 of conductive foam conformable to body surfaces. The sheet 18 carries on its exterior surface 20 an elongated, flexible strip 22. The sheet 18 of conductive foam and flexible strip 22 are held together by electrical terminal means formed from a conductive male snap fastener member, generally designated 26, which includes a lower circular plate portion 28, from the center of which a hollow stud 30 projects upwardly and an upper plate portion 32 mounted on the upper surface of the strip 22, the upper plate portion having an upwardly protruding hollow socket portion 34 receiving the stud 30. In addition, a layer 31 of adhesive can be used to secure the strip 22 to the conductive foam 18. Preferably the width of the flexible strip is at least equal to the width of the flexible foam so that when the strip is placed around a body member, as described below, the entire sheet of foam is uniformly held against a body surface.

The sheet of foam and the strip are assembled and held together by placing the sheet 18 of flexible foam underneath the flexible strip 22, and if desired, placing a layer 31 of adhesive between the flexible foam and the strip, and centrally locating and aligning the upper plate portion 32 with its upwardly protruding hollow socket portion 34 on the exterior surface of the strip 22. The stud 30 is inserted through a centrally located aperture 36 in the foam and an aligned aperture through the flexible sheet 22 into the socket 34. The pressing together of the snap fastener portions causes the upper end of the stud 30 to fold inwardly and its side walls to collapse outwardly, whereupon the snap fastener parts are tightly wedged together.

Preferably the sheet 18 of conductive foam is flexible to the extent of readily conforming to body surfaces of the patient to whom it is applied without any portion of the surface losing contact with the skin. Moreover, preferably the conductive foam is hypoallergenic and porous so as to substantially eliminate any allergic reaction due to the application of the electrode to the skin of the patient and avoid skin maceration caused by moisture build up.

The layer 18 of conductive foam can be manufactured from polyurethane foam material containing finely divided conductive particles such as finely divided carbon particles. The conductive foam requires a low resistivity to provide a low current density path to complete the electrosurgical circuit and minimize tissue heating at the foam/skin interface. Preferably, the layer of foam has a resistivity less than about 4,000 ohm-cm, and more preferably a resistivity of less than about 2,500 ohm-cm.

The surface area of the sheet of conductive foam is sufficiently large to provide enough contact with the skin to prevent undue heating of the skin. The surface area required depends upon the resistivity of the foam, the amount of current being used at the active electrode, and the length of time the active electrode is continuously used during surgery. Determination of the proper surface area for the conductive foam is within the skill of the art.

The male snap fastener 26 serves as the electrical terminal means. The exterior portion of the male snap fastener, which comprises the hollow socket 34 and the portion of the stud 30 extending above the strip 22, forms the exterior terminal part of the electrode. This part of the electrode is attached to the electrosurgical generator during surgery so as to form a detachable electrical connection.

While it is preferred that the electrical terminal means 26 be formed from stainless steel since stainless steel male snap fasteners are readily available, this invention is not limited to the use of stainless steel. The electrical terminal may be fabricated of any conductive material such as aluminum, copper, silver, silver/silver chloride, brass, platinum, gold and the like. The conductive material can, for instance, be only present as a plating on a substrate of, for example, another metal, plastic or the like.

The flexible strip 22 may be formed from a single layer, but it is found that better results are obtained by providing a laminated strip comprising an inner layer 38 of a nonstrechable plastic material as, for example, polyester film, and an outer layer 40 of a flexible, plastic-impregnated paper such as latex-impregnated paper. The inner layer, being of smooth surface, makes comfortable contact with body surfaces, and being non-stretchable, prevents forced enlargement during surgery with loss of contact between the conductive foam 18 and body surfaces. The outer layer being of plastic-impregnated paper, is receptive to a marking medium as, for example, writing inks, typewriter and addressograph impressions. Thus it can be used to receive an identification or other marking as required.

The length of the strip depends upon which body member the electrode 16 is to be attached. For example, a substantially longer strip is required for attaching the electrode to the trunk than if the electrode is to be attached to a wrist. To provide maximum versatility, preferably the strip is of sufficient length to go around the trunk of an adult. If a shorter strip is desired, it is easy for operating room personnel to cut the strip to the desired length.

With reference to FIG. 3, on the exterior surface 42 of the end 44 of the strip, there is an adhesive layer or surface 46 protected prior to application of the electrode with removable sheet means, a preferred form of which is shown in the drawings as a paper tab or sheet 48 having a release surface of silicone or other release material disposed in coextensive engagement with the adhesive surface 46. The adhesive used for the adhesive surface 46 is one to which the interior surface 51 of the inner band 38 of the strip is susceptible to adherence, such as a synthetic acrylic copolymer.

As shown in FIGS. 2 and 3, the conductive foam 18 is secured to the flexible strip 22 closer to the end 44 having the adhesive surface 46 than it is to the opposite end 50. This is because the strip is provided in a length longer than may be required to be attached to body area of small circumference such as the wrist or forearm, and the excess portion of the strip is then separated from the electrode.

If desired, the lower circular plate portion 28 of the male snap fastener 26 can be spaced apart from the body to prevent direct contact between the highly conductive plate 28 and body surfaces. This separation can be effected by a layer 52 of conductive foam as shown in FIG. 3, or by a nonconductor such as a plug of rigid or flexible plastic.

Figure 4:
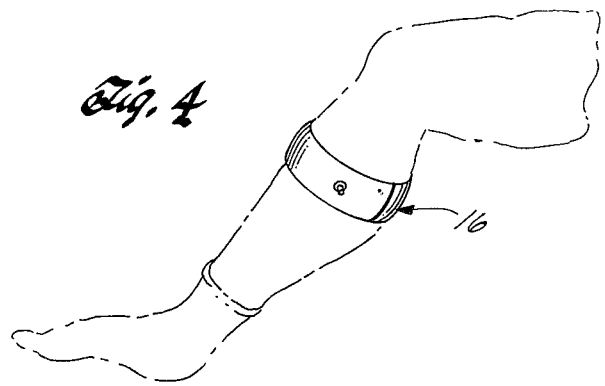
FIG. 4 is a view of the electrode of FIG. 2 mounted on the leg of a patient.

Application of the electrode is readily effected by first rubbing the area of the skin to which the electrode is to be applied with an abrasive. This operation has the effect of removing a layer of dead cells from the skin area. This removal enhances the electrical connection to be effected and is preferable as a dry pretreatment which is consistent with the dry construction and operation of the electrode 16 itself. Abrasive pretreatment is often performed together with sterilization of the skin by swabs containing alcohol and pumice. It will be understood that abrasive pretreatment of the skin, whether wet or dry, is not at all essential to the pretreatment. Next, the layer of conductive foam 18 is pressed onto the abraded skin area. Then a portion of the flexible strip 22 is tightly wound around the body member, such as a leg, as shown in FIG. 4 to which the electrode is to be attached until the interior surface 51 of the inner layer 38 can be pressed against the adhesive layer 46. The excess portion of the strip 22 is then cut away so it does not interfere with the surgical procedure. Attachable electrical connection is then made between the electrosurgical generator 10 and the electrical terminal means provided by the hollow socket portion 34 and the hollow stud 30 of the male snap fastener 26.

From the above description, it is evident that an electrode according to the present invention is of simple construction, easy to apply, efficient in operation and economical to manufacture. Since the construction of the electrode is dry and application can be effected dry without use of electrolytes, elaborate packaging is not required. Potential for skin irritation is minimized because an electrolyte gel is not required and there is no direct contact between skin and adhesive.

Other advantages of the electrode are that it is relatively small in size; easily contoured to various body surfaces, thus allowing many sites for application; disposable; readily and securely attached to the body without restricting circulation; capable of maintaining good and stable electrode/skin contact for long periods of time; and capable of being presterilized and prepackaged, if desired.

Exemplary of an electrode embodying features of this invention and having the above-mentioned advantages is one having a sheet 18 of conductive foam formed of polyurethane foam loaded with sufficient fine carbon particles to have a resistivity of about 2,000 ohm-cm. The foam is square-shaped, 2 inches per side, and has a thickness of 0.150 inch. The sheet 18 of foam is bonded to the underside 51 of a 2 inch by 20 inch flexible strip 22 at a position 2 inches from the end 44 of the strip having an adhesive layer 46. The strip comprises two layers laminated together, an interior layer 38 of 2.5 mil thick polyester film sold by DuPont under the trademark "Mylar". The exterior layer 40 is a 2.5 mil thick sheet of latex impregnated paper. The adhesive layer 31 between the foam 28 and Mylar layer 38 is an adhesive capable of bonding polyurethane to polyester such as Fasson-S277 sold by Avery Products, Inc. of San Marino, Cal.

The adhesive layer 46 is a pressure sensitive adhesive. The adhesive layer is protected by a sheet 48 of silicone coated release paper. The electrical terminal means comprises a male snap fastener 26, the components 28, 30, 32 and 34 of which are made of stainless steel. The lower circular plate portion 28 has a diameter of 0.56 inches. The stud 30 has an outside diameter of 0.12 inch and a height of 0.3 inch. The upper circular plate portion 32 has a diameter of 0.56 inch and a socket barrel outside diameter of 0.155 inch and an inside diameter of 0.115 inch.

Although this invention has been described in considerable detail with reference to certain versions thereof, other versions of the invention are within the scope of this invention. For example, although the sheet of conductive foam has been described as being square with dimensions of 2 inches per side, the sheet 18 can assume other shapes and sizes. With respect to size, the contact area provided by the sheet of conductive foam should not be greatly reduced in order to assure a low resistance connection, while size increase is limited only by practical considerations. Circular and rectangular shaped variations are specifically contemplated as well as elliptical shapes and any others considered desirable.

Because of variations such as these, the spirit and scope of the appended claims should not necessarily be limited to the description of the preferred embodiments.

What is claimed is:

1. An indifferent electrode for use in electrosurgical procedures with an electrosurgical generator without the use of an electrolyte, the electrode comprising:
    (a) a sheet of conductive foam conformable to body surfaces and having an exterior surface and an opposed interior surface, the interior surface of the sheet of foam providing direct contact with body surfaces;
    (b) an electrical terminal means carried by the sheet of conductive foam, the electrical terminal means forming an exterior terminal part of the electrode with which a detachable electrical connection with the electrosurgical generator can be effected; and
    (c) an elongated flexible strip secured to the exterior surface of the sheet of conductive foam for attachment around a body member for maintaining the interior surface of the sheet of conductive foam in direct contact with body surfaces, the strip having an interior surface facing the sheet of conductive foam and an opposed exterior surface, at least a portion of the exterior surface of the strip having an adhesive surface, wherein the interior surface of the strip is susceptible to adherence to the adhesive surface.

2. The electrode of claim 1 in which the sheet of conductive foam comprises polyurethane foam.

3. The electrode of claim 2 in which the sheet of conductive foam comprises fine conductive particles.

4. The electrode of claim 3 in which the fine conductive particles are carbon particles.

5. The electrode of claim 1, in which the sheet of conductive foam comprises fine conductive particles.

6. The electrode of claim 5 in which the conductive particles are carbon particles.

7. The electrode of claim 1 in which the sheet of conductive foam has a resistivity less than about 4,000 ohm-cm.

8. The electrode of claim 1 in which the sheet of conductive foam has a resistivity less than about 2,500 ohm-cm.

9. The electrode of claim 1 including nonconductive means for mounting the terminal means spaced apart from body surfaces.

10. The electrode of claim 1 in which the terminal means comprises a metallic snap fastener element.

11. An indifferent electrode for use in electrosurgical procedures with an electrosurgical generator without the use of electrolytes, the electrode comprising:
  (a) a sheet of polyurethane foam filled with fine carbon particles to render it conductive, the sheet being conformable to body surfaces and having an exterior surface and an opposed interior surface, the interior surface of the sheet providing direct contact with body surfaces, the sheet of foam having a resistivity less than about 2,500 ohms-cm;
  (b) electrical terminal means carried by the sheet of conductive foam, the electrical terminal means comprising a metallic snap fastener element forming an exterior terminal part of the electrode with which a detachable electrical connection with the electrosurgical generator can be effected; and
  (c) an elongated flexible strip secured to the exterior surface of the sheet of conductive foam for mounting around a body member for maintaining the entire interior surface of the sheet of conductive foam in direct contact with body surfaces, the strip having an interior surface facing the sheet of conductive foam and an opposed exterior surface, the exterior surface of one end of the strip having an adhesive surface, wherein the interior surface of the strip is susceptible to adherence to the adhesive surface, and wherein the strip is secured to the exterior surface of the sheet of conductive foam such that the sheet of conductive foam is closer to the end of the strip having the adhesive surface.

12. The electrode of claim 11 including nonconductive means for mounting the electrical terminal means spaced apart from body surfaces.

* * * * *